United States Patent [19]
Heck et al.

[11] Patent Number: 4,921,857
[45] Date of Patent: May 1, 1990

[54] 4-OXO-4H-QUINOLIZINE-3-CARBOXYLIC ACIDS AND DERIVATIVES THEREOF

[75] Inventors: James V. Heck, Scotch Plains; Eugene D. Thorsett, Fanwood, both of N.J.

[73] Assignee: Merck & Co., Inc., Rahway, N.J.

[21] Appl. No.: 98,117

[22] Filed: Sep. 18, 1987

[51] Int. Cl.$^5$ ............................................. C07D 455/02
[52] U.S. Cl. ....................................... 514/254; 514/247
[58] Field of Search ............... 514/254, 210, 211, 212, 514/218, 222, 227, 228, 230, 241, 247, 252, 256, 277–306, 254

[56] References Cited

U.S. PATENT DOCUMENTS 4,479,947 10/1984 Christensen .......................... 424/203
4,650,804 3/1987 Kitaura et al. ....................... 514/306
4,698,349 10/1987 Kitaura et al. ....................... 514/306

FOREIGN PATENT DOCUMENTS 0157346 10/1985 European Pat. Off. .

OTHER PUBLICATIONS

Kato et al., "Synthesis of Methylpyridine Derivatives XVII" Chem. Pharm. Bull. 22(4): 744–751 (1974).
Y. Sato, "The Synthesis of Lupine Alkaloids II, The Syntheis of 1-(α-Piperidyl)quinolizidine," Pharm. Bull., 5, 412–416 (1957).
G. Buchmann & W. Duchna, "Beitragzur Synthese von 1,3-disubstituierten 4H-Chinolizonen-(4)auf Basis Pyridyl-2-acetonitril," Pharmazie, 23, 301–303(1968)(Ger.).

Primary Examiner—H. M. S. Sneed
Assistant Examiner—James Saba
Attorney, Agent, or Firm—Richard S. Parr; Michael S. Sudol

[57] ABSTRACT

This invention relates to a method of treating bacterial infections with 4-oxo-4H-quinolizine-3-carboxylic acids and derivatives thereof. This invention further relates to pharmaceutical compositions that are useful in the treatment of bacterial infections.

8 Claims, No Drawings

4-OXO-4H-QUINOLIZINE-3-CARBOXYLIC ACIDS AND DERIVATIVES THEREOF

BACKGROUND OF THE INVENTION (a) Field of the Invention

This invention relates to certain 4-oxo-4H-quinolizine-3-carboxylic acids and derivatives thereof (also known as quinolizinones) that are useful in the treatment of bacterial infections. In particular, this invention relates to a method of treating bacterial infections with said compounds. This invention further relates to pharmaceutical compositions containing said compounds and to a method of treating bacterial infections with said pharmaceutical compositions.

A multitude of broad spectrum antibiotics useful in the treatment of both Gram-positive and Gram-negative bacterial infections, as well as other microbial infections, are known. However, a continuing need for new antibiotics exists. For example, known antibiotics may be effective against only certain strains of microorganisms. Furthermore, and perhaps more seriously, continued widespread use can give rise to resistant strains of microorganisms against which a particular antibiotic or group of antibiotics was previously effective. The compounds of this invention were discovered as part of a search for new antibiotics intended to overcome such problems.

(b) Prior Art

Certain quinolizinone carboxylic acid derivatives are known. For example, Y. Kitaura et al., European Patent application 0157346, have disclosed compounds of Formula A:

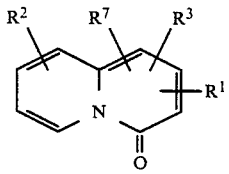

wherein $R_1$ is inter alia carboxy or cyano; $R^7$ is hydrogen or aryl; $R^2$ is hydrogen, hydroxy, lower alkyl, or lower alkoxy; and $R^3$ is inter alia hydrogen, hydroxy, lower alkyl, lower alkoxy, and optionally substituted aryl; and wherein $R^2$ and $R_3$ can be located at any position in the quinolizinone ring. The compounds are reported to exhibit antiallergy and antiulcer activities. The European patent application, however, neither discloses nor suggests antibacterial activity.

SUMMARY OF THE INVENTION

This invention relates to certain quinolizinones that are useful in the treatment of bacterial infections. In particular, this invention relates to a method of treating bacterial infections with compounds of Formula I. This invention further relates to pharmaceutical compositions containing said compounds of Formula I and to a method of treating bacterial infections with said pharmaceutical compositions.

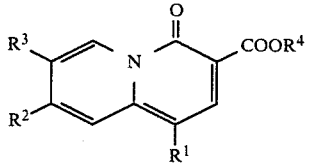

wherein $R^1$ is:
(a) $C_1$–$C_6$ alkyl;
(b) $C_2$–$C_6$ alkenyl;
(c) fluorinated $C_1$–$C_6$ alkyl;
(d) $C_3$–$C_7$ cycloalkyl;
(e) phenyl or phenyl substituted with one or more substituents selected from the group consisting of:
  (i) $C_1$–$C_6$ alkyl;
  (ii) halogen;
  (iii) hydroxy;
  (iv) $C_1$–$C_6$ alkoxy; and
  (v) $NR^5R^6$, or a pharmaceutically acceptable acid addition salt thereof, wherein $R^5$ and $R^6$ are independently hydrogen or $C_1$–$C_6$ alkyl, or wherein $R^5$ and $R^6$ taken together are $C_2$–$C_6$ alkylene; or
(f) monocyclic or bicyclic heteroaryl of 5 to 10 ring atoms wherein 1 to 4 of the ring atoms are independently N, O, or S and the rest are carbon, and wherein one or more hydrogen atoms attached to the heteroaryl ring atoms may optionally be replaced with substituents selected from the group consisting of:
  (i) $C_1$–$C_6$ alkyl;
  (ii) halogen;
  (iii) hydroxy;
  (iv) $C_1$–$C_6$ alkoxy; and
  (v) $NR^7R^8$, or a pharmaceutically acceptable acid addition salt thereof, $R^7$ and $R^8$ are independently hydrogen or $C_1$–$C_6$ alkyl, or wherein $R^7$ and $R^8$ taken together are $C_2$–$C_6$ alkylene;

$R^2$ is:
(a) halogen;
(b) $C_1$–$C_6$ alkoxy;
(c) monocyclic or bicyclic heteroaryl of 5 to 10 ring atoms wherein 1 to 4 of the ring atoms are independently N, O, or S and the rest are carbon, and wherein one or more hydrogen atom attached to the heteroaryl ring atoms may optionally be replaced with substituents selected from the group consisting of:
  (i) $C_1$–$C_6$ alkyl;
  (ii) halogen;
  (iii) hydroxy;
  (iv) $C_1$–$C_6$ alkoxy; and
  (v) $NR^9R^{10}$, or a pharmaceutically acceptable acid addition salt thereof, wherein $R^9$ and $R^{10}$ are independently hydrogen or $C_1$–$C_6$ alkyl, or wherein $R^9$ and $R^{10}$ taken together are $C_2$–$C_6$ alkylene;
(d) $NR^{11}R^{12}$, or a pharmaceutically acceptable acid addition salt thereof, wherein $R^{11}$ and $R^{12}$ are independently hydrogen or $C_1$–$C_6$ alkyl; or

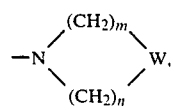

or a pharmaceutically acceptable acid addition salt thereof, wherein W is CH$_2$O, S, or NR$^{13}$, wherein R$^{13}$ is hydrogen or C$_1$-C$_6$ alkyl, and wherein m and n are independently integers of from 1 to 3;

R$^3$ is:
(a) hydrogen;
(b) halogen; or
(c) C$_1$-C$_6$ alkoxy; and

R$^4$ is:
(a) hydrogen;
(b) C$_1$-C$_6$ alkyl;
(c) a pharmaceutically acceptable cation; or
(d) a prodrug ester group.

The term "C$_1$-C$_6$ alkyl" refers to straight or branched chain aliphatic hydrocarbon groups having from 1 to 6 carbon atoms, also referred to as lower alkyl. Examples of C$_1$-C$_6$ alkyl are methyl, ethyl, propyl, butyl, pentyl, hexyl, and the isomeric forms thereof.

The term "C$_2$-C$_6$ alkenyl" refers to straight or branched chain hydrocarbon groups having from 2 to 6 carbon atoms and possessing one carbon-carbon double bond. Examples of C$_2$-C$_6$ alkenyl are vinyl; allyl; 2- or 3-butenyl; 2-, 3-, or 4-entenyl; 2-, 3-, 4-, or 5-hexenyl; and isomeric forms thereof.

The term "C$_1$-C$_6$ fluorinated alkyl" refers to C$_1$-C$_6$ alkyl in which one or more hydrogen atoms are replaced with fluorine atoms. Examples of C$_1$-C$_6$ fluorinated alkyl are fluoromethyl, difluormethyl, trifluoromethyl, 1- or methyl, difluoromethyl, trifluoromethyl. 1 or 2-fluoroethyl, 1,1 difluoroethyl, 2,2,2-trifluoroethyl, perfluoroethyl; other similarly monofluoroinated, polyfluorinated, and perfluorinated ethyl, propyl, butyl, pentyl, and hexyl groups; and the isomeric forms thereof.

The term "C$_3$-C$_7$ cycloalkyl" refers to saturated monocyclic hydrocarbon groups having from 3 to 7 carbon atoms in the ring. Examples of C$_3$-C$_7$ cycloalkyl are cyclopropyl, cyclobutyl, cyclopentyl, cyclohexyl, and cycloheptyl.

The terms "C$_1$-C$_6$ alkoxy" refers to straight or branched chain alkyl oxy groups having from 1 to 6 carbon atoms. Examples of C$_1$-C$_6$ alkoxy are methoxy, ethoxy, propoxy, butoxy, pentyloxy, hexyloxy, and the isomeric forms thereof.

The term "C$_2$-C$_6$ alkylene" refers to aliphatic hydrocarbon chains substituted at two different carbon atoms. Examples of C$_2$-C$_6$ alkenyl are —(CH$_2$($_2$—, —(CH$_2$)$_3$—, —(CH$_2$)$_4$—, —(CH$_2$)$_5$—, —(CH$_2$)$_6$—, and —(CH$_2$)($_7$—, as well as the isomeric forms thereof. As used herein, C$_2$—C$_6$ alkylene chains are taken with nitrogen atoms to form 1-azacycloalkyl groups: 1-azacyclopropyl, 1 azacyclobutyl, 1-azacyclopentyl, 1-azacyclohexyl, and 1-azacycloheptyl.

The term "monocyclic or bicyclic heteroaryl" refers to aromatic ring systems havinq from 5 to 10 nuclear ring atoms, of which from 1 to 4 nuclear ring atoms are independently N, O, or S and the rest are carbon. Monocyclic heteroaryl groups have one aromatic ring. Examples of monocyclic heteroaryl include 1- , 2- , or 3-pyrrolyl; 1-, 2-, or 4-imidazolyl; 2- or 3-thienyl; 2 or 3-furanyl; 2-, 3- or 4-pyridinyl; 2 or 4-pyrimidinyl; s-triazinyl; 3-, 4-, or 5-isoxazolyl; 3-, 4-, or 5-isothiazolyl; and other such groups known in the art. Bicyclic heteroaryl groups have two fused aromatic rings or a nonaromatic ring fused to an aromatic ring. Examples of bicyclic heteroaryl include various groups derived from indole, isoindole, indolizine, indazole, purine, quinoline, isoquinoline, quinolizine, phthalazine, quinoxaline, quinazoline, cinnoline, pteridine, benzofuran, isobenzofuran, benzo[b]thiophene, benzo[c]thiophene, indoline, isoindoline, chroman, isochroman, chromene, and other such groups known in the art.

The term "pharmaceutically acceptable acid addition salt" refers to a salt prepared from a compound of Formula I in which substituent R$^2$ contains a basic nitrogen atom. Said salts may be prepared by contacting such nitrogen-containing compounds of Formula I with an inorganic or organic acid whose anion is generally considered suitable for human consumption or by using other methods known in the art, such as ion exchange. Examples of pharmaceutically acceptable acid addition salts include the acetate, adipate, alginate, aspartate, benzoate, benzenesulfonate, bisulfate, butyrate, citrate, camphorate, camphorsulfonate, cyclopentane-propionate, dodecylsulfate, ethanesulfonate, fumarate, glucoheptanoate, gluconate, glycerophosphate, heptanoate, hexanoate, hydrochloride, hydrobromide, hydroiodide, 2-hydroxyethanesulfonate, lactate, maleate, maleate, methanesulfonate, 2-naphthalenesulfonate, nicotinate, pamoate, pectinate, 3-phenylpropionate, phosphate, pivalate, propionate, succinate, sulfate, tartrate, thiocyanate, tosylate, and undecanoate salts.

The term "pharmaceutically acceptable cation" refers to a positively charged inorganic or organic ion that is generally considered suitable for human consumption. Examples of pharmaceutically acceptable cations are hydrogen, alkali metal (lithium, sodium, and potassium), magnesium (½ Mg$^{++}$), calcium (½ Ca$^{++}$), ammonium, alkylammonium, dialkylammonium, trialkylammonium, tetraalkylammonium, diethanolaminium, triethanolaminium, and guanidinium ions, and protonated forms of lysine, benzathine, procaine, and choline. Cations may be interchanged by methods known in the art, such as ion exchange. Where compounds of Formula I are prepared in the carboxylic acid form (that is, where R$^4$ is hydrogen ion), addition of a base form of the cation (such as a hydroxide or a free amine) will yield the appropriate cationic form.

The term "prodrug ester group" refers to any one of several ester-forming groups that are hydrolyzed under physiological conditions. Examples of prodrug ester groups include pivaloyloxymethyl, acetoxymethyl, phthalidyl, indanyl, and methoxymethyl, as well as other such groups known in the art, including those described in detail in the U.S. Pat. No. 4,479,947, which is incorporated herein by reference.

Examples of halogen are fluorine, chlorine, bromine, and iodine.

It is also understood that the compounds of Formula I may form hydrates or other solvates from the solvents in which they are prepared or from which they are crystallized. These hydrates or other solvates may be used per se or they may be dehydrated or desolvated by heating (for example, at about 70° C. to 100° C.) in vacuo.

DESCRIPTION OF THE INVENTION

The compounds of this invention may be prepared by methods illustrated in the following Schemes. Unless otherwise specified, the various substituents are defined as for Formula I, above. Scheme A illustrates the preparation of compounds of Formula VI (that is, Formula I wherein R$^4$ is C$_1$-C$_6$ alkyl) and Formula VII (that is, Formula I wherein R$^4$ is hydrogen).

SCHEME A

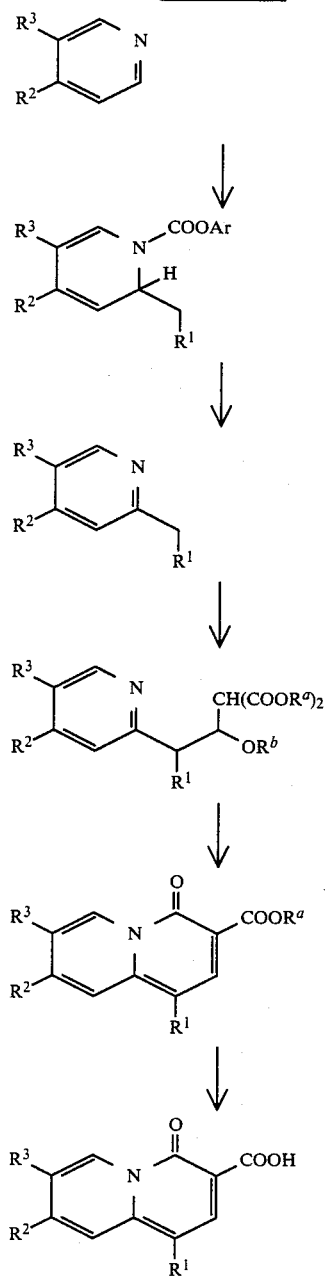

Precursor pyridine derivatives of Formula II can be converted to 2-substituted pyridine derivatives of Formula IV using any of various methods known in the art. A preferred method involves dihydropyridine intermediates of Formula III. A mixture of a compound of Formula II in a suitable organic solvent is activated by adding a suitable acylating reagent. The activated pyridine reaction mixture is then treated with a suitable organo-metallic reagent of the formula $R^1CH_2M$, wherein $R^1$ is defined as above for Formula I and M is a suitable metal moiety. Suitable organic solvents for the reaction sequence are organic liquids in which the various reactants can be dissolved or suspended but which are otherwise chemically inert. Examples of suitable organic solvents include alkanes and cycloalkanes; ethers and cyclic ethers, such as diethyl ether, tetrahydrofuran, tetrahydropyran, and dioxane; aromatic hydrocarbons, such as benzene, toluene, and xylene; and other organic liquids known in the art. A preferred organic solvent is tetrahydrofuran. Suitable acylating reagents are acyl compounds that are sufficiently reactive to activate pyridines of Formula II for subsequent reaction with the organometallic reagents and which form sufficiently labile N acyl groups to facilitate later formation of compounds of Formula IV. Preferred acylating reagents include various haloformate derivatives. Examples of suitable haloformate derivatives include alkyl haloformates, such as methyl chloroformate, ethyl chloroformate, and isopropyl chloroformate; aryl haloformates, such as phenyl chloroformate and naphthyl chloroformate; aralkyl haloformates, such as benzyl chloroformate; and other haloformates known in the art. A preferred haloformate reagent is phenyl chloroformate. Suitable metals or substituted metal moieties are those substances known in the art that render the organometallic reagent of the formula $R^1CH_2M$ capable of alkylating the activated pyridines. Examples of suitable groups M are MgX (wherein X is halogen), Cu(I), and Li. A preferred group M is MgCl.

Dihydropyridine intermediates of Formula III may be aromatized to pyridine derivatives of Formula IV using any of several oxidation methods known in the art. A preferred oxidation method employs 2,3-dichloro-5,6-dicyanobenzoquinone (DDQ) in a suitable organic solvent. Suitable organic solvents for oxidation with DDQ are organic liquids in which the various reagents can be dissolved or suspended and in which the oxidation with DDQ can take place but which are otherwise chemically inert. Examples of suitable organic solvents include alkanes and cycloalkanes; cyclic ethers, such as tetrahydrofuran, tetrahydropyran, and dioxane; aromatic hydrocarbons, such as benzene, toluene, and xylene; and other solvents known in the art. A preferred organic solvent is benzene.

Pyridine derivatives of Formula IV can be converted to quinolizinones of Formula VI using methods known in the art. A preferred method involves malonate derived intermediates of Formula V. A compound of Formula IV in a suitable organic solvent is metallated with a suitable strong base. The metallated substance is then allowed to react with an alkoxymethylidene malonate diester of the formula $R^bOCH=C(COOR^a)_2$, wherein $R^a$ is $C_1$–$C_6$ alkyl or aralkyl such as benzyl and $R^5$ is $C_1$–$C_6$ alkyl. Suitable organic solvents for the reaction sequence are organic liquids in which both the metallation and subsequent alkylation can occur but which are otherwise chemically inert. Examples of suitable organic solvents include alkanes and cycloalkanes; ethers and cyclic ethers, such as diethyl ether, tetrahydrofuran, tetrahydropyran, and dioxane; aromatic hydrocarbons, such as benzene, toluene, and xylene; and other solvents known in the art. A preferred organic solvent is tetrahydrofuran. Suitable strong bases are substances that are sufficiently basic to facilitate the subsequent reaction with $R^bOCH=C(COOR^a)_2$ but which do not form significant quantities of byproducts through side reactions. Suitable strong bases include alkali metal alkyls, such as n-butyllithium and t-butyllithium; alkali metal salts of amines, such as lithium diisopropylamide and lithium hexamethyl disilazide; alkali metal hydrides, such as lithium hydride, sodium hydride, and potassium hydride; and other strong bases known in the art. A preferred strong base is n-butyllithium.

Compounds of Formula V are cyclized and aromatized to form quinolizinones of Formula VI (that is, Formula I wherein $R^4$ is $C_1$–$C_6$ alkyl) by thermally induced condensation and elimination reactions in a suitable organic solvent or in the absence of solvent. Suitable organic solvents are organic liquids in which the compounds can be dissolved or suspended and which can be heated to sufficiently high temperature for the reaction sequence to occur. Examples of suitable organic solvents include higher boiling alcohols, such as butanol, octanol, and the like; aromatic hydrocarbons, such as toluene and xylene; N,N-disubstituted amides, such as dimethylformamide and dimethylacetamide; and other organic liquids known in the art. A preferred organic solvent is xylene.

Hydrolysis of esters of Formula VI using methods known in the art produces free carboxylic acids of Formula VII (that is, Formula I wherein $R^4$ is hydrogen) or salts thereof. Preferred hydrolysis methods include acid- or base-catalyzed hydrolysis. Basic hydrolysis can be used to prepare salt forms of Formula VII directly. Various salts can be prepared from the free carboxylic acid by addition of an appropriate base or by other methods known in the art, such as ion exchange. Cations may be exchanged by various methods, particularly ion exchange.

Free carboxylic acids of Formula VII or salts thereof may also be converted to prodrug ester forms by any of several esterfication methods known in the art.

An alternative method for preparing amino quinolizinones of Formula X (that is, Formula VII wherein $R^2$ is $NR^{11}R^{12}$) is illustrated in Scheme B.

SCHEME B

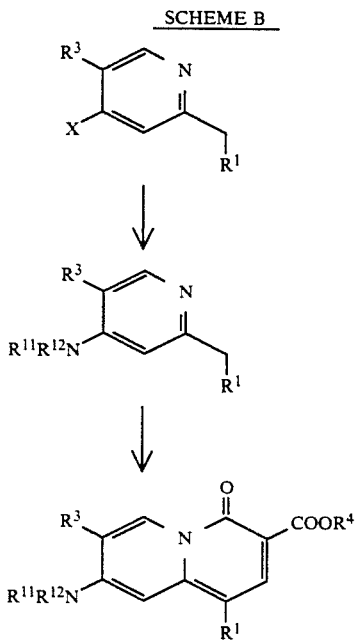

Using methods described above for Scheme A, compounds of Formula II in which $R^2$ is halogen or $C_1$–$C_6$ alkoxy can be converted to pyridine derivatives of Formula VIII (that is, Formula IV in which $R^2$ is X) wherein X is halogen (preferably fluorine or chlorine) or $C_1$–$C_6$ alkoxy. Reaction of compounds VIII with an appropriate amine of the formula, wherein $R^{11}R^{12}NH$, wherein $R^{11}$ and $R^{12}$ are defined as for Formula I, in a suitable organic solvent or in the absence of a separate solvent yields aminopyridines of Formula IX. Suitable organic solvents are organic liquids in which the various reactants can be dissolved or suspended and in which the amination reaction is facilitated but which are otherwise chemically inert. Examples of suitable organic solvents include alkanols, such as methanol, ethanol, propanol, and the like; alkanes and cycloalkanes; ethers and cyclic ethers, such as diethyl ether, tetrahydrofuran, tetrahydropyran, and dioxane; aromatic hydrocarbons, such as benzene, toluene, and xylene; heteroaromatic solvents, such as pyridine and lutidine; N,N-disubstituted amides, such as dimethylformamide and dimethylacetamide; N-substituted lactams, such as N-methylpyrrolidinone and N-methylpiperidinone; and other organic liquids known in the art. Preferred reaction conditions employ no solvent other than the amine $R^{11}R^{12}NH$.

Compounds of Formula IX are then converted to amino quinolizinones of Formula X (that is, Formula I wherein $R^2$ is $R^{11}R^{12}N$) using methods described above in Scheme A.

The preferred embodiments of this invention are methods and pharmaceutical compositions that employ compounds of the following general formula:

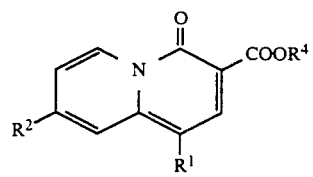

wherein $R^1$ is phenyl or phenyl substituted with one or more substituents selected from the group consisting of $C_1$–$C_6$ alkyl, halogen, hydroxy, $C_1$–$C_6$ alkoxy, and $NR^5R^6$ (wherein $R^5$ and $R^6$ are defined as for Formula I); $R^2$ is $NR^{11}R^{12}$ (wherein $R^{11}$ and $R^{12}$ are defined as for Formula I), or $$-N\diagup\!\!\!\diagdown W$$

(wherein W is $NR^{13}$, wherein $R^{13}$ is $C_1$–$C_6$ alkyl; and wherein $R^4$ is hydrogen, $C_1$–$C_6$ alkyl, or a pharmaceutically acceptable cation.

The most preferred embodiments of this invention are methods and pharmaceutical compositions that employ the compound of the following formula:

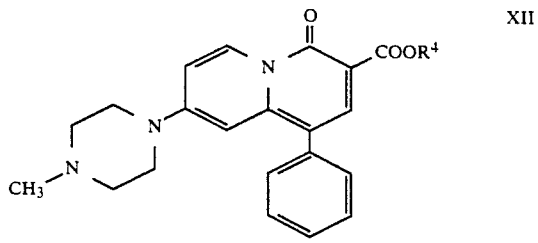

wherein $R^4$ is hydrogen or $C_1$–$C_6$ alkyl.

The compounds of the present invention exhibited antibacterial activity against various Gram-positive and Gram-negative bacteria. Representative pathogens that are sensitive to the antibacterial agents of this invention include various species of Escherichia and Klebsielaa. The antibacterial activities of the compounds illustrated in the Examples were tested by the following method.

Agar Diffusion Assay for Antibacterial Activity

A stock solution of each test compound was prepared at a concentration of 1.28 mg/ml using sterile distilled water. After initial solubilization, two-fold dilutions were prepared and added as one-ml portions to $15 \times 100$ mm petri plates. A nine-ml portion of trypticase soy agar (TSA) was melted and added to each plate. The test compound and agar were mixed and allowed to cool. Final concentrations of compound was 128 µg/ml and lower, according to the dilutions used. Controls were prepared using norfloxacin, coumermycin A-1, or novobiocin, and solvent.

Each plate was inoculated using a multipoint inoculator with $10^5$ colony-forming units (cfu) of the appropriate bacterium. Each bacterium was stored at $-70°$ C. before use and cultured in trypticase soy broth (TSB) at 35° C. for 18 hours. The cultures, containing ca. $10^9$ cfu/ml, were diluted as necessary with TSB to provide concentrations of $10^5$ cuf/inoculation spot. The test plates were then incubated at 35° C. for 20 hours. Minimum inhibitory concentrations (MIC) for each compound was the lowest concentration that allowed no growth, a barely visible haze, or five or fewer discrete colonies. Results for the compound of Example 4 are listed in Table I.

TABLE I

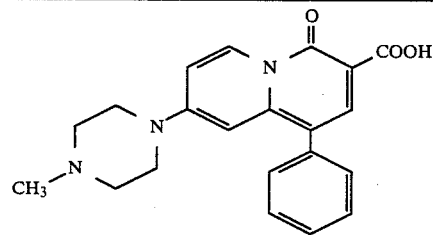

| Organism[a] | Strain (MB No.) | Minimum inhibitory conc. (µg/ml) |
|---|---|---|
| St. aur | 2865 | 128 |
| E. coli. | 2891 | 1.0 |
| E. coli. | 5157 | 8.0 |
| K. pneu. | 4005 | 8.0 |
| Ps. aer. | 5160[b] | >128 |

[a]Abbreviation:
St. aur. = Staphylococcus aureus:
E. coli. = Escherichia coli:
K. pneu. = Klebsiella pneumoniae:
Ps. aer. = Pseudomonas aeruginosa
[b]Norfloxacin-resistant strain The compounds and pharmaceutical compositions of the present invention are valuable antibacterial agents active against various Gram-positive and Gram-negative bacteria and accordingly find utility in human and veterinary medicine. The antibacterials of this invention are not limited to utility as medicaments; they may be used in all manner of industry, for example, as additives to animal feed, as preservatives of food, as disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in white water of paper mills to inhibit the growth of harmful bacteria.

Regardless of the route of administration selected, pharmaceutically effective amounts of the compounds of the present invention are formulated into pharmaceutically acceptable dosage forms by conventional methods known to those skilled in the art. The compounds may also be formulated using pharmaceutically acceptable acid or base addition salts where appropriate. Moreover, the compounds or their salts may be used in a suitable hydrated form. The compounds of this invention may be used in any of a variety of pharmaceutical preparations. The compounds may be administered in such oral dosage forms as tablets, capsules, pills, powders, granules, elixirs, or syrups. The compounds may also be administered intravascularly, intraperitoneally, subcutaneously, intramuscularly, or topically using forms known to the pharmaceutical art.

Compositions for injection, a preferred route of delivery, may be prepared in unit dosage form or in multidose containers. The compositions may take such forms as suspensions, solutions, or emulsions in oily or aqueous vehicles, and may contain formulatory agents. Alternatively, the active ingredient may be in powder form of reconstitution at the time of delivery with a suitable vehicle, such as sterile water. Topical applications may be formulated in hydrophobic or hydrophilic bases as ointments, creams, lotions, paints, or powders.

For the orally administered pharmaceutical compositions and methods of the present invention, the foregoing active ingredients will typically be administered in admixture with suitable pharmaceutical diluents, excipients, or carriers (collectively referred to herein as "carrier" materials) suitably selected with respect to the intended form of administration, that is, oral tablets, capsules, elixirs, syrups, and the like, and consistent with conventional pharmaceutical practices. For example, for oral administration in the form of tablets or capsules, the active drug components may be combined with any oral non toxic pharmaceutically acceptable inert carrier such as lactose, starch, sucrose, cellulose, magnesium stearate, dicalcium phosphate, calcium sulfate, mannitol, and the like, or various combinations thereof; for oral administration in liquid form, the active drug components may be combined with any oral non-toxic pharmaceutically acceptable inert carrier such as water, saline, ethanol, polyethylene glycol, propylene glycol, corn oil, cottonseed oil, peanut oil, sesame oil, benzyl alcohol, various buffers, and the like, or various combinations thereof Moreover, when desired or necessary, suitable binders, lubricants, disintegrating agents, and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes, or combinations thereof. Lubricants for use in these dosage forms include boric acid, sodium benzoate, sodium acetate, sodium chloride, and the like, or combinations thereof. Disintegrators include without limitation, starch, methylcellulose, agar, bentonite, guar gum, and the like, or combinations thereof. Sweetening and flavoring agents and preservatives can also be included where appropriate.

The dosage to be administered depends to a large extent upon the condition and size of the subject being treated as well as the route and frequency of administration, the parenteral route by injection being preferred for generalized infections. Such matters, however, are left to the routine discretion of the therapist according to principles of treatment well known in the antibacterial art. In general, a daily dosage consists of from about 5 to about 500 mg of active ingredient per kg of body weight of the subject in one or more treatments per day. A preferred daily dosage for adult humans lies in the range of from about 5 to 300 mg of active ingredient per kg of body weight. Another factor influencing the precise dosage regimen, apart from the nature of the infection and peculiar identity of the individual being treated, is the molecular weight of the chosen species of this invention.

The compositions for human deliver per unit dosage, whether liquid or solid, may contain from 0.1% to 99% of active material, the preferred range being from about 10–60%. The composition will generally contain from about 15 mg to about 1500 mg of the active ingredient; however, in general, it is preferable to employ a dosage amount in the range of from about 250 mg to 2000 mg. In parenteral administration, the unit dosage is usually the pure compound of Formula I in sterile water solution or in the form of a soluble powder intended for such a solution.

The preferred method of administration of the antibacterial agent of Formula I is parenteral by i.v. infusion, i.v. bolus, or i.m. injection.

For adults, 5–300 mg of Formula I antibacterial per kg of body weight given 2, 3, or 4 times per day is preferred. Preferred dosage is 250 mg to 2000 mg of the antibacterial agent of Formula I given two (b.i.d.), three (t.i.d.), or four (q.i.d.) times per day. More specifically, for mild infections, particularly of the urinary tract, a dose of 250 mg t.i.d. or q.i.d. is recommended. For moderate infections against highly susceptible gram positive and gram negative organisms, a dose of 1000 mg t.i.d. or q.i.d. is recommended. For severe, life threatening infections against organisms at the upper limits of sensitivity to the antibiotic, a dose of 2000 mg t.i.d. or q.i.d. is recommended.

For children, a dose of 5 100 mg/kg of body weight given 2, 3, or 4 times per day is preferred; a dose of 50 mg/kg t.i.d. or q.i.d. is usually recommended.

The following examples further illustrate details for the preparation of the compounds of this invention. The invention, which is set forth in the foregoing disclosure, is not to be construed or limited either in spirit or in scope by these examples. Those skilled in the art will readily understand that known variations of the conditions and processes of the following preparative procedures can be used to prepare these compounds. All temperatures are degrees Celsius unless otherwise noted.

DESCRIPTION OF THE PREFERRED EMBODIMENTS

EXAMPLE 1

2-Benzyl 4-chloropyridine

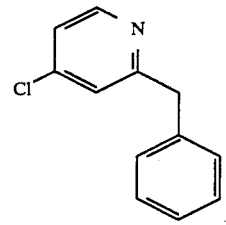

A solution of 4 chloropyridine (2.50 g) in tetrahydrofuran is chilled to 40°. Phenyl chloroformate (2.8 ml) is then added dropwise, and the resulting thick slurry is warmed to −20°. A solution of 1M benzylmagnesium chloride in tetrahydrofuran (22 ml) is added dropwise, taking care to maintain the temperature below 0°. Upon completion of the addition, the cooling bath is removed and the reaction allowed to warm to room temperature. The reaction is then treated with 50% saturated aqueous ammonium chloride and diluted with diethyl ether (200 ml). The organic phase is washed with 1N hydrochloric acid (50 ml) and 1M disodium hydrogen phosphate (50 ml). Drying and concentration of the organic phase affords the intermediate 2-benzyl-1-carbophenoxy-1,2-dihydropyridine as an oil (7.2 g).

The crude dihydropyridine intermediate is dissolved in benzene (100 ml) and heated to 65°. A solution of 2,3-dichloro 5,6-dicyanobenzoquinone (5.0 q) in warm benzene (50 ml) is added dropwise with stirring. The reaction mixture is stirred at 65° for one hour and then cooled to room temperature. The mixture is washed with 10% aqueous sodium bicarbonate (two portions of 100 ml each) and water (100 ml), then extracted with 2N hydrochloric acid (two portions of 150 ml each). The combined acid extracts are made alkaline with dilute aqueous sodium hydroxide and extracted with diethyl ether. After drying and concentration, the title compound is obtained as an oil (0.95 g) that can be further purified by chromatography on silica gel (using 4:1 by volume hexane-ethyl acetate as eluent). Structure assignment is confirmed by nmr spectroscopy. nmr (CDCl$_3$): δ (ppm) 4.16 (s, 2H); 7.14–7.40 (m, 7H); 8.46 (d, 1H).

EXAMPLE 2

2-Benzyl-4-(4-methyl-1-piperazinyl)pyridine

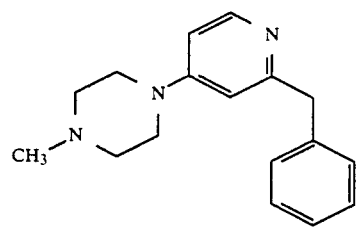

A mixture of 2-benzyl-4-chloropyridine (0.480 q; see Example 1) and N-methylpiperazine (1.0 ml) is heated at 125° under an inert atmosphere for 17 hours. Upon cooling to room temperature, the mixture produces a crystalline mass. The crude solid is treated with saturated aqueous potassium carbonate (5 ml), water (2 ml), diethyl ether (5 ml) and dichloromethane (5 ml). The organic layer is separated, dried and concentrated to an oil. Excess N-methylpiperazine is removed by drying the oil at 45° under high vacuum (10 torr), giving the title compound as a viscous oil. Structure assignment is confirmed by nmr spectroscopy. nmr (CDCl$_3$): δ (ppm) 2.34 (s, 3H); 2.48 (dd, 4H); 3.28 (dd, 4H); 4.07 (s, 2H); 6.5 (m, 3H); 7.26 (m, 4H); 8.22 (d, 1H).

EXAMPLE 3

Ethyl-8-(4-methyl-1-piperazinyl)-4-oxo-1-phenyl-4H-quinolizine-3-carboxylate

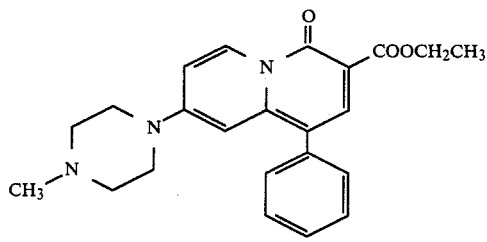

A solution of 2-benzyl-4-(4-methyl-1-piperazinyl) pyridine (0.122 q; see Example 2) in tetrahydrofuran (1.5 ml) is cooled to -65°. A solution of 2.5 M n-butyllithium in hexane (0.20 ml) is added dropwise and the resulting red-brown slurry is stirred for 15 minutes at −65°. A solution of diethyl ethoxymethylenemalonote (0.115 ml) in tetrahydrofuran (0.38 ml) is then added dropwise over 10 minutes, after which the reaction is stirred an additional 10 minutes at −65° and 30 minutes at −20°. The reaction is quenched by the addition of acetic acid (0.029 ml) and warmed to room temperature. The reaction mixture is diluted with diethyl ether (5 ml) and washed with water. The organic phase is concentrated to an oil that is then dissolved in xylene (1 ml) and heated to 170° in a sealed tube. After 40 minutes the reaction is cooled to room temperature and the solution decanted from a small amount of tar. Removal of the solvent under vacuum affords a mixture of crystals and a dark oil. Trituration with 1:1 (by volume) diethyl ether-petroleum ether removes the oily contaminant and filtration yields the crystalline title ester (0.073 q), m.p. 165°-168°. Structure assignment is confirmed by nmr spectroscopy. nmr (CDCl$_3$): δ (ppm) 1.38 (t, 3H); 2.32 (s, 3H); 2.5 (dd, 4H); 3.4 (dd, 4H); 4.38 (q, 2H); 6.72 (d, 1H); 6.86 (dd, 1H); 7.3–7.5 (m, 5H); 8.10 (s, 1H); 9.34 (d, 1H).

EXAMPLE 4

8-(4-Methyl-1-piperazinyl)-4-oxo-1-phenyl-4H-quinolizine-3-carboxylic acid

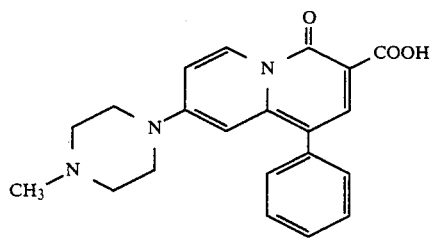

To a solution of the title ester of Example 3 (0.050 g) in methanol (1.0 ml) is added water (0.25 ml) and 1 M aqueous sodium hydroxide (0.25 ml). The reaction is kept at 55° for three hours and then concentrated. Water (0.5 ml) is added to the concentrate and the solution is adjusted to pH 4.5–5.0 with acetic acid. The resultant precipitate is extracted with chloroform and the organic extract is dried and concentrated. Trituration of the residue with diethyl ether yields the product as a crystalline solid (0.032 g), m.p. 212°–214° (dec). Structure assignment is confirmed by nmr spectroscopy. nmr (CDCl$_3$): δ (ppm) 2.34 (s, 3H); 2.52 (dd, 4H); 3.46 (dd, 4H): 6.81 (br d, 1H); 6.99 (dd, 1H): 7.3–7.55 (br m, 5H); 8.19 (s, 1H); 9.18 (d, 1 H).

What is claimed is:

1. A method for treating bacterial infections comprising administering to a patient in need of such treatment a pharmaceutically effective amount of at least one compound having the formula:

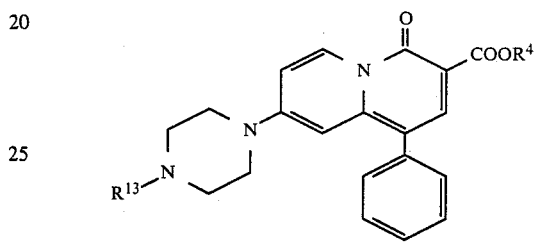

wherein R$^4$ is:
(a) hydrogen; or
(b) C$_1$–C$_6$-alkyl; and
R$^{13}$ is C$_1$–C$_6$-alkyl.

2. A method according to claim 1 wherein R$^{13}$ is methyl.

3. A method according to claim 2 wherein the compound is ethyl 8-(4-methyl-1-piperazinyl)-4-oxo-1-phenyl-4H-quinolizine-3-carboxylate.

4. A method according to claim 2 wherein the compound is 8-(4-methyl-1-piperazinyl)-4-oxo-1-phenyl-4H-quinolizine-3-carboxylic acid.

5. An antibacterial composition for treating bacterial infections comprising a pharmaceutically effective amount of at least one compound having the formula:

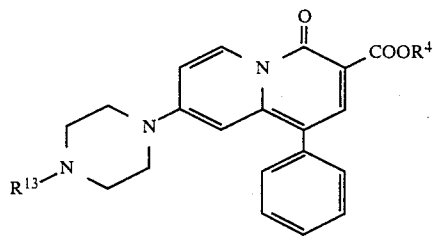

wherein R$^4$ is:
(a) hydrogen; or
(b) C$_1$–C$_6$-alkyl; and
R$^{13}$ is C$_1$–C$_6$-alkyl
and one or more pharmaceutically acceptable carriers.

6. A pharmaceutical composition according to claim 5 wherein said compound selected from the group consisting of:
ethyl 8-(4-methyl-1-piperazinyl)-4-oxo-1-phenyl-4H-quinolizine-3-carboxylate, and
8-(4-methyl-1-piperazinyl)-4-oxo-1-phenyl-4H-quinolizine-3-carboxylic acid.

7. A method for treating bacterial infections comprising administering a pharmaceutically effective amount of a pharmaceutical composition of claim 5 to a patient in need of such treatment.

8. A method according to claim 7 wherein the compound of said pharmaceutical composition is selected from the group consisting of:
- ethyl 8-(4-methyl-1-piperazinyl)-4-oxo-1-phenyl-4H-quinolizine-3-carboxylate, and
- 8-(4-methyl-1-piperazinyl)-4-oxo-1-phenyl-4H-quinolizine-3-carboxylic acid.

* * * * *